US010835509B2

(12) United States Patent
Howard et al.

(10) Patent No.: US 10,835,509 B2
(45) Date of Patent: *Nov. 17, 2020

(54) PREVENTION AND/OR TREATMENT OF NEURODEGENERATIVE DISEASE

(71) Applicant: Howard Foundation Holdings Ltd, Cambridgeshire (GB)

(72) Inventors: Alan Norman Howard, Cambridgeshire (GB); John Nolan, Waterford (IE); Riona Mulcahy, Waterford (IE)

(73) Assignee: HOWARD FOUNDATION HOLDINGS LTD., Cambridgeshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,083

(22) Filed: May 15, 2018

(65) Prior Publication Data
US 2019/0167624 A1 Jun. 6, 2019

(30) Foreign Application Priority Data
Dec. 4, 2017 (GB) .................................. 1720119.5

(51) Int. Cl.
  *A61K 31/202* (2006.01)
  *A61K 31/07* (2006.01)
  *A61K 31/201* (2006.01)
  *A61K 31/047* (2006.01)
  *A61P 25/28* (2006.01)

(52) U.S. Cl.
  CPC .......... *A61K 31/202* (2013.01); *A61K 31/047* (2013.01); *A61K 31/07* (2013.01); *A61K 31/201* (2013.01); *A61P 25/28* (2018.01)

(58) Field of Classification Search
  CPC .... A61K 31/202; A61K 31/047; A61K 31/07; A61K 31/201; A61P 25/28
  USPC ....................................................... 514/560
  See application file for complete search history.

(56) References Cited

U.S. PATENT DOCUMENTS

| 2005/0163873 | A1  | 7/2005 | Ritch ............................ 424/752 |
| 2006/0166935 | A1* | 7/2006 | Bryhn .................. A61K 31/202 514/78 |
| 2014/0187648 | A1* | 7/2014 | Howard ............... A61K 31/047 514/729 |
| 2016/0051490 | A1* | 2/2016 | Deshpande ............ A61K 31/07 514/567 |
| 2016/0067203 | A1* | 3/2016 | Takenaka ............. A61K 31/202 514/560 |

FOREIGN PATENT DOCUMENTS

| GB | 2483121 A | 2/2012 |
| GB | 2503608 A | 1/2014 |
| WO | WO 2006/116755 A2 | 11/2006 |
| WO | WO 2009/078716 A1 | 6/2009 |
| WO | WO 2013/005037 A1 | 1/2013 |
| WO | WO 2014/014766 A1 | 1/2014 |
| WO | WO 2017/144443 A1 | 8/2017 |

OTHER PUBLICATIONS

Wang et al. Nutritional biomarkers in Alzheimer's disease: the association between carotenoids, n-3 fatty acids, and dementia severity. (Journal of Alzheimer's disease 13, 2008, 31-38).*
Huang et al. Oral supplementation of lutein/zeaxanthin and omega-3 long chain polyunsaturated fatty acids in persons aged 60 years or older, with or without AMD. Invest Ophthalmol. Vis. Sci. 2008; 49: 3864-3869.*
Nakawatase et al. "Alzheimer's Disease and Related Dementias." Cecil's Textbook of Medicine. (Twenty-First Edition, vol. 1): W.B. Saunders Company, 2000. p. 2042-2045.*
Greicius et al. "Presenile Dementia Syndrome: An Update on Taxonomy and Diagnosis." Journal of Neurol. Neurosurg. Psychiatry, 2002; 72: 691-700.*
Gauthier et al. "Alzheimer's Disease: Current Knowledge, Management and Research." Can. Med. Assoc. J. 1997; 157(8): 1047-1052.*
Gasparini et al. "Peripheral Markers in Testing Pathophysiological Hypothese and Diagnosing Alzheime's Disease." FASEB. J. 12, 1998: 17-34.*
Koike et al. Concentration of triglyceride docosahexaenoic acid by lipase hydrolysis in a lecithin-W/O microemulsion. (Asian Pacific Confederation of Chemical Engineers congress program and abstracts, Session ID: 3P-01-065; 2004).*
Pallas et al. From aging to Alzheimer's disease: unveiling "the switch" with the senescence-accelerated mouse model (SAMP8). Journal of Alzheimer's Disease, 15, 2008, 615-624.*
Shinto et al J. Alzheimers disease, 2014, 38(1) pp. 1-16 (Year: 2014).*
Ademowo et al., Free radical biology and medicine 2017, 108, 77-85 (Year: 2017).*
United Kingdom Search Report dated Jan. 19, 2018, issued to GB 1720119.5.
Written Opinion of the International Searching Authority dated Jun. 28, 2018, issued to International Application No. PCT/GB2018/051255.
John M. Nolan, et al., "The Impact of Supplemental Macular Carotenoids in Alzheimer's Disease: A Randomized Clinical Trial," Journal of Alzheimer's Disease, vol. 44, Feb. 19, 2015, pp. 1157-1169.

(Continued)

*Primary Examiner* — Yevgeny Valenrod
(74) *Attorney, Agent, or Firm* — Stein IP, LLC

(57) ABSTRACT

A method for the prevention and/or treatment of dementia in a human subject; the method comprising the step of administering an effective amount of a composition comprising at least one carotenoid selected from the group consisting of lutein, zeaxanthin and meso-zeaxanthin; and a composition comprising at least one omega-3 fatty acid.

22 Claims, 5 Drawing Sheets

(56) References Cited

OTHER PUBLICATIONS

Rebecca Power et al., "Supplemental Retinal Carotenoids Enhance Memory in Healthy Individuals With Low Levels of Macular Pigment in a Randomized, Double Blind, Placebo-Controlled Clinical Trial," Poster Presentations, Alzheimer's & Dementia: The Journal of the Alzheimer's Association, Jul. 19, 2017, p. 1567.

Elizabeth Johnson, A possible role for lutein and zeaxanthin in cognitive function in the elderly, 2012, The American Journal of Clinical Nutrition, vol. 96, No. 5.

United Kingdom Search Report dated Nov. 8, 2018, issued to Great Britain Application No. GB1807590.3.

* cited by examiner

PREVENTION AND/OR TREATMENT OF NEURODEGENERATIVE DISEASE

CROSS-REFERENCE TO RELATED APPLICATIONS

This application claims the benefit of priority to United Kingdom Application No. 1720119.5, filed Dec. 4, 2017, in the Intellectual Property Office. All disclosures of the document named above are incorporated herein by reference.

FIELD OF THE INVENTION

The present invention relates to the use of combinations of substances for the prevention and/or treatment of neurodegenerative disease, especially dementia, in human subjects.

BACKGROUND OF THE INVENTION

Alzheimer's disease (AD) is the most common type of dementia, followed by vascular dementia. In the UK, the number of people with AD is 850,000 and in the USA is 5.5 million. With increasing age and population, it is anticipated that the overall prevalence of the disease will continue to increase [ref. 1]. Despite considerable research effort, the cause of the disease is still unknown but established risk factors include age, family history of disease and education [ref. 1] and putative risk factors include cigarette smoking, physical inactivity and social isolation [ref. 32]. The effectiveness of current pharmacological treatments (medications) is strictly limited and varies among individuals. Moreover, the effect of current medications is at best only palliative, as they cannot halt disease progression. The UK NHS suggests, as preventative, the following: cessation of smoking, limiting alcohol consumption, a healthy well balanced diet, staying physically and mentally active.

There have been numerous studies on the effects of the Mediterranean Diet, a diet characterised by a high intake of vegetables, olive oil, and a moderate intake of fish, dairy products and wine. There is a consensus that adherence to such diets is associated with better cognitive performance [refs. 2-7] and a reduced risk of dementia, especially AD [refs. 8-12], but no clear evidence of the exact foodstuffs responsible.

Some studies have pointed to an effect from omega-3 fatty acids, of which docosahexaenoic acid (DHA) is found in high concentration in fish oil and in fatty fish such salmon and herring. There is a substantial concentration of DHA in the human brain where it forms a structural component within this neural tissue. High consumption of omega-3 fatty acids is associated with better cognitive performance [ref. 13] and a reduced risk of dementia [refs. 14-17]. However, interventional studies have shown conflicting results, with some demonstrating improvements in cognition [refs. 18, 19] and others demonstrating no beneficial effect [refs. 20, 21].

Other food items of interest include the carotenoids lutein (L) and zeaxanthin (Z). These carotenoids, which are dietary of origin are found in certain fruits and vegetables (e.g. spinach, broccoli, peppers, melon) [ref. 22]. In humans, L and Z are found in high concentrations in the eye (specifically the centre part of the retina known as the macula, where they are referred to as "macular pigment" or "macular carotenoids") and brain [refs. 23, 24]. High carotenoid intake has been found to result in a reduced risk of AD [refs. 25,-27]. Some studies administering L and Z have shown improvement in different domains of cognition [refs. 28, 29], while another randomised trial showed no benefit [ref. 30].

Another macular carotenoid is meso-zeaxanthin (MZ), which is a stereoisomer of zeaxanthin. The chemical structures of L, Z and MZ are shown in FIG. 1.

Vitamin E is also present in the brain, and high plasma concentrations of vitamin E have been associated with a reduced risk of AD [ref. 31]. There have been no reports of successful treatment of AD following administration of this vitamin.

In summary, there is general agreement that there are substances in the brain which play a role in preventing AD, but attempts so far to identify and/or use them have been unsuccessful.

Compositions comprising all three macular carotenoids (L, Z and MZ) are commercially available as nutritional supplements. One example of such a supplement is sold under the trade mark Macushield®, and consists of capsules containing the three macular carotenoids L, Z and MZ in the amounts of 10 mg, 2 mg and 10 mg, respectively, per capsule. WO 2013/005037 discloses the use of such a composition for improving the visual performance of a human subject, the composition optionally further comprising a fish oil and/or an omega 3 fatty acid. US2016/0067203 (Lion Corporation) discloses and claims compositions for improving cognitive function, the compositions comprising docosahexaenoic acid (DHA) in combination with lutein, zeaxanthin and capsanthin.

The specification includes the results of a "Passive Avoidance Test" performed using mice fed the test composition or a control composition for 3 months (see especially Example 5 in Table 2 of the prior art document). The mice were given a mild electric shock when they went into a darkened compartment, and learned to avoid the darkened compartment when the test was repeated. The prior art specification also presents data (Table 3) suggesting that the amount of amyloid 13 protein in the brain was reduced in the test mice compared to the controls (although the numbers of animals involved in this experiment were very small, n=3 and n=4), so these results are not statistically significant.

There are no data from experiments with human subjects. Also, there is no evidence that the exemplified composition could improve cognitive function in, or stabilise the condition of, subjects already suffering from cognitive impairment.

WO2006/116755 (Trustees of Tufts College) discloses and claims a composition having "*synergistic amounts of lutein and DHA for use in improvement of cognitive function*". The claims are based on a trial in which 50 human subjects (all female) were given daily supplements, over a 4 month period, containing (i) a placebo; or (ii) DHA or lutein; or (iii) DHA and lutein in combination. Various cognitive function tests were performed at start and end of the period of supplementation, and the results are shown in Table 2 of the prior art document. All compositions, except the placebo, gave statistically significant (<0.05) improvements in a verbal fluency test (hence, there was no evidence of any synergy between the DHA and lutein).

In addition however, subjects given the DHA/lutein combination demonstrated statistically significant improvements in a Shopping List Memory Test and an MIR ("Memory-in-Reality") Apartment Test. However for the latter, it is clear from FIG. 4 of the prior art publication that the baseline score was unusually low for that group, so a big improvement was perhaps nothing to do with the supplementation. Finally, there is no evidence to show that the DHA/lutein combination could have any positive effect on subjects already experiencing cognitive impairment.

SUMMARY OF THE INVENTION

The inventors have found that the macular carotenoids such as a mixture of meso-zeaxanthin (MZ), lutein (L) and zeaxanthin (Z), or omega-3 fatty acids, given separately, have no effect individually on the progression of dementia, but when given together are remarkably and surprisingly effective in halting or retarding the progression of the disease, and improving cognitive function.

Accordingly, in a first aspect, the present invention provides a composition comprising at least one carotenoid selected from the group consisting of lutein, zeaxanthin and meso-zeaxanthin; and a composition comprising at least one omega-3 fatty acid; for use in the prevention and/or treatment of dementia in a human subject.

More especially the composition/s is/are for use in the prevention and/or treatment of Alzheimer's disease.

In a second aspect the prevention provides a method for the prevention and/or treatment of dementia, especially Alzheimer's disease, in a human subject, the method comprising the step of administering to a human subject an effective amount of a composition comprising at least one carotenoid selected from the group consisting of lutein, zeaxanthin and meso-zeaxanthin; and an effective amount of a composition comprising at least one omega-3 fatty acid.

In one embodiment, in the first and second aspects of the invention, the at least one carotenoid comprises lutein. In one embodiment, the at least one carotenoid comprises any combination of at least two of the aforesaid carotenoids (i.e. L & Z, L & MZ, or Z & MZ). Preferably one of the aforementioned "at least two carotenoids" comprises lutein. In a preferred embodiment, in the first and second aspects of the invention, a composition is used which comprises each of lutein, zeaxanthin and meso-zeaxanthin.

More preferably, in the first and second aspects of the invention, a composition is used which comprises lutein, zeaxanthin, meso-zeaxanthin and at least one omega-3 fatty acid, such that all four of the aforementioned substances can be obtained by a human subject by the administration of a single composition, and this represents the preferred embodiment of the invention.

If two separate compositions (i.e. one composition for the at least one carotenoid and one composition for the at least one omega-3 fatty acid) are used, these are desirably administered substantially simultaneously (i.e. within 5 minutes of one another), or at least concurrently (i.e. on the same day). If two separate compositions are employed in performance of the invention, these are preferably both administered to the subject via the same route (preferably both administered orally), although administration of one composition by a first route and administration of the other composition by a second route is envisaged as a possibility.

In the first or second aspect of the invention the composition or compositions (as appropriate) may be administered by any suitable route to a human subject including, for example, intra-venous administration. Preferably however the composition is administered orally, and advantageously the composition is formulated so as to be suitable for oral administration.

The composition or compositions (as appropriate) may be administered to a human subject who is not yet exhibiting any symptoms of dementia (e.g. Alzheimer's disease), with a view to preventing the subject from developing dementia, or with a view to deferring the time at which the subject starts to exhibit one or more of the symptoms of dementia, (e.g. Alzheimer's disease). Either of these may be regarded as "preventing" dementia or, specifically, Alzheimer's disease—in the first instance indefinitely, and in the second instance for at least a period of time. The period of time for which the onset of one or more of the symptoms of dementia/Alzheimer's disease may be deferred may depend on the age of the subject when the composition is administered, and on other factors which influence the susceptibility of the subject to dementia (e.g. genotype, diet, smoking history etc.). Preferably the onset of the one or more symptoms of dementia is deferred for at least 6 months, more preferably at least 12 months, and most preferably at least 18 months. In particular, the one or more symptoms of dementia typically comprise or consist of cognitive impairment (which may be assessed by MMSE, discussed below). The inventors believe that administration of one or more macular carotenoids and one or more omega-3 polyunsaturated fatty acids (especially DHA and/or eicosapentaenoic acid, EPA) in sufficient amounts, to a human subject who is not yet exhibiting any symptoms of Alzheimer's disease, could prevent the occurrence of Alzheimer's disease in the subject indefinitely.

Alternatively, the composition may be administered to a subject who is already exhibiting one or more symptoms of dementia (especially Alzheimer's disease), with a view to preventing or retarding the progression of the disease. Preventing the progression of the disease means that the severity of the existing one or more symptoms of dementia does not increase. In particular, preventing the progression of the disease will preferably comprise or consist of substantially preventing progression of cognitive impairment in the subject. Retarding the progression of the disease means that the severity of the symptoms increases more slowly than would have been the case if intervention (i.e. administering the composition of the invention) had not occurred. Preventing or retarding the progression of the dementia (e.g. Alzheimer's disease) is regarded as treating the disease for present purposes.

Diagnosing dementia is known to be challenging. A useful diagnostic aid is the mini mental state examination or "MMSE" (Tombaugh & McIntyre 1992 J. Am. Geriatr. Soc. 40, 922-935). For present purposes, a subject can be considered to have dementia if they obtain an MMSE score of 25 or less and where any other causes of cognitive impairment (e.g. head injury, chronic alcohol abuse, fever, urinary tract infections etc.) can be excluded.

Preventing progression of cognitive impairment in a subject, as a result of administering the composition in accordance with the invention, may be checked by performing a mini mental state examination. In preferred embodiments, a subject already suffering from dementia (i.e. having an MMSE score of 25 or less) and consuming a composition in accordance with the invention will experience a reduction in MMSE score of no more than 2 points over an 18 month period, more preferably no more than 1 point over an 18 month period, and most preferably a zero point reduction over an 18 month period.

As noted previously, the composition comprises at least one omega-3 fatty acid. For present purposes, unless the context dictates otherwise, the term "fatty acid" is intended also to encompass not only the free acid but also derivatives of fatty acids, such derivatives encompassing in particular esters, especially esters formed with glycerol (monoglycerides, diglycerides and, preferably, triglycerides), and salts. Preferred salts are those containing monocations, such as $Na^+$, $K^+$ or $NH_4^+$. Most preferred salts are those comprising metallic monocations. The free fatty acid or the triglyceride is the most preferred form of the compound.

The omega-3 fatty acid component of the composition preferably comprises an omega-3 polyunsaturated fatty acid or derivative thereof, most preferably docosahexaenoic acid (DHA) or a derivative thereof. The composition may contain two or more omega-3 fatty acids. The composition may comprise eicosapentaenoic acid (EPA). In one embodiment the composition comprises both DHA and EPA.

A convenient source of omega-3 fatty acids is fish oil. Accordingly, in a preferred embodiment, the composition comprises fish oil. Since fish oil has quite a strong odour, it may be preferred to use deodourised fish oil, which is commercially available. Another source of omega-3 fatty acids is nut oil. Without being bound by any particular theory, the inventors believe that DHA is the most active omega-3 fatty acid in terms of preventing and/or treating dementia. Nut oil does not contain substantial amounts of DHA and therefore is not preferred for the purposes of the present invention.

Other sources of fatty acids include algae (see Ji et al, 2015 "Omega-3 Biotechnology: A green and sustainable process for omega-3 fatty acids production" Front Bioeng. Biotechnol. 3, 158).

The composition may be formulated in a 'bulk' form, to be admixed, for example, with a conventional foodstuff, including dairy foodstuffs (e.g. incorporated into butter or ice cream) or non-diary foodstuffs (e.g. margarine, vegetable stock or fish-stock preparations). More preferably however the composition is formulated in unit dosage form, preferably one suitable for oral consumption by a human subject, including a tablet, capsule, gel, liquid, powder or the like. The one or more macular carotenoids may be granulated, for example as microcapsules, before inclusion in the formulation.

Conveniently, but not necessarily, the composition may be packaged in a foil blister pack, of the sort known to those skilled in the art. Desirably one or two of the doses are taken each day, the amount of active agents in the doses being adjusted accordingly.

The composition may conveniently comprise conventional diluents, especially vegetable oils such as sunflower, safflower, corn oil and rape seed oils, excipients, bulking agents and the like which are well known to those skilled in the art. Such substances include, calcium and/or magnesium stearate, starch or modified starch. Other conventional formulating agents may be present in the composition, including any one or more of the following non-exhaustive list: acidity regulators; anticaking agents (e.g. sodium aluminosilicate, calcium or magnesium carbonate, calcium silicate, sodium or potassium ferricyanide), antioxidants (e.g. vitamin E, vitamin C, polyphenols), colorings (e.g. artificial colorings such as FD&C Blue No. 1, Blue No. 2, Green No. 3, Red No. 40, Red No. 3, Yellow No. 5 and Yellow No. 6; and natural colorings such as caramel, annatto, cochineal, betanin, turmeric, saffron, paprika etc.); color retention agents; emulsifiers; flavours; flavour enhancers; preservatives; stabilizers; sweeteners and thickeners.

Other optional ingredients of the composition include vitamins and/or minerals. Preferably the composition comprises vitamin E. Preferably the composition comprises at least one B vitamin. Preferably the composition comprises vitamin E and at least one B vitamin.

Typically the composition or compositions (as appropriate) is/are administered at least once a week, preferably at least twice a week, more preferably three times a week, and most preferably daily. In a typical embodiment at least one unit dosage form of the composition is taken on a daily basis. The person skilled in the art will appreciate that the frequency of consumption can be adjusted to take account of the concentration of active agents (one or more macular carotenoids, omega-3 fatty acid), present in the formulation. The administration of the composition can be adjusted accordingly.

Preferably, in order to prevent the onset of one or more symptoms of dementia, the composition should be administered to subjects at or before the age of 50, before which age the onset of dementia is rather rare.

In order to obtain a preventative effect, the composition should preferably be administered, typically at least 2 or 3 times a week, or daily, over a period of at least 6 months, preferably over a period of at least 12 months, and even more preferably over a period of at least 18 months. For treatment of patients already exhibiting one or more symptoms of dementia, the composition should preferably be administered indefinitely, for as long as the patient is able to take the composition.

For present purposes the "active agents" in the composition are considered to be the one or more macular carotenoids and the at least one omega-3 fatty acid.

The precise concentration of the active agents in the composition of the invention is not critical: a beneficial effect on the subject can be obtained by consuming larger doses of a composition comprising lower concentrations of active agents, or vice versa.

If the macular carotenoid composition includes two or more carotenoids, their respective ratio in the composition is not thought to be critical and can vary quite widely. For example, the percentage of either MZ or lutein in the composition can range from 10% to 90% (of the macular carotenoid present in the composition). The percentage of zeaxanthin can typically range from about 5 to 45% (of the macular carotenoid present in the composition). One particular composition has an MZ:lutein:zeaxanthin ratio of 10:10:2 (or 45%, 45%, 10%), but this is not essential. Another typical composition has a ratio (MZ:L:Z) of 12:10:2.

One preferred composition for use in performance of the invention is in unit dosage form, with each unit dose comprising 10 mg meso-zeaxanthin, 10 mgs lutein, 2 mgs zeaxanthin and fish oil (preferably 1 gm of fish oil).

Another preferred composition for use in performance of the invention is in unit dosage form with each unit dose comprising 15 mgs meso-zeaxanthin, 5 mgs lutein, 1 mg zeaxanthin and fish oil (preferably 1 gm fish oil).

Desirably an average daily dose of the composition provides a total macular carotenoid content of up to, but not exceeding, 100 mg, preferably up to, but not exceeding, 75 mg, and most preferably up to, but not exceeding, 50 mg. Desirably the average daily dose of the composition provides a minimum total macular carotenoid content of at least 18 mg, more preferably at least 20 mg, and most preferably at least 22 mg. Such concentrations are known to be well-tolerated with substantially no adverse effects.

Advantageously, the average daily dose of the composition provides an amount of omega-3 fatty acid in the range 10 mg to 2 gms, more preferably in the range 20 mgs to 2 gms, and most preferably in the range 25 mgs to 1 gram.

The foregoing omega-3 fatty acid content may be provided entirely by DHA, or by a combination of two or more omega-3 fatty acids, one of which is preferably DHA. DHA desirably constitutes at least 50% of the omega-3 fatty acid content of the composition, preferably at least 55%, more preferably at least 60%, and most preferably at least 65%.

The invention will now be further described by way of illustrative example and with reference to the accompanying drawings, in which.

EXAMPLE

Figure 1:
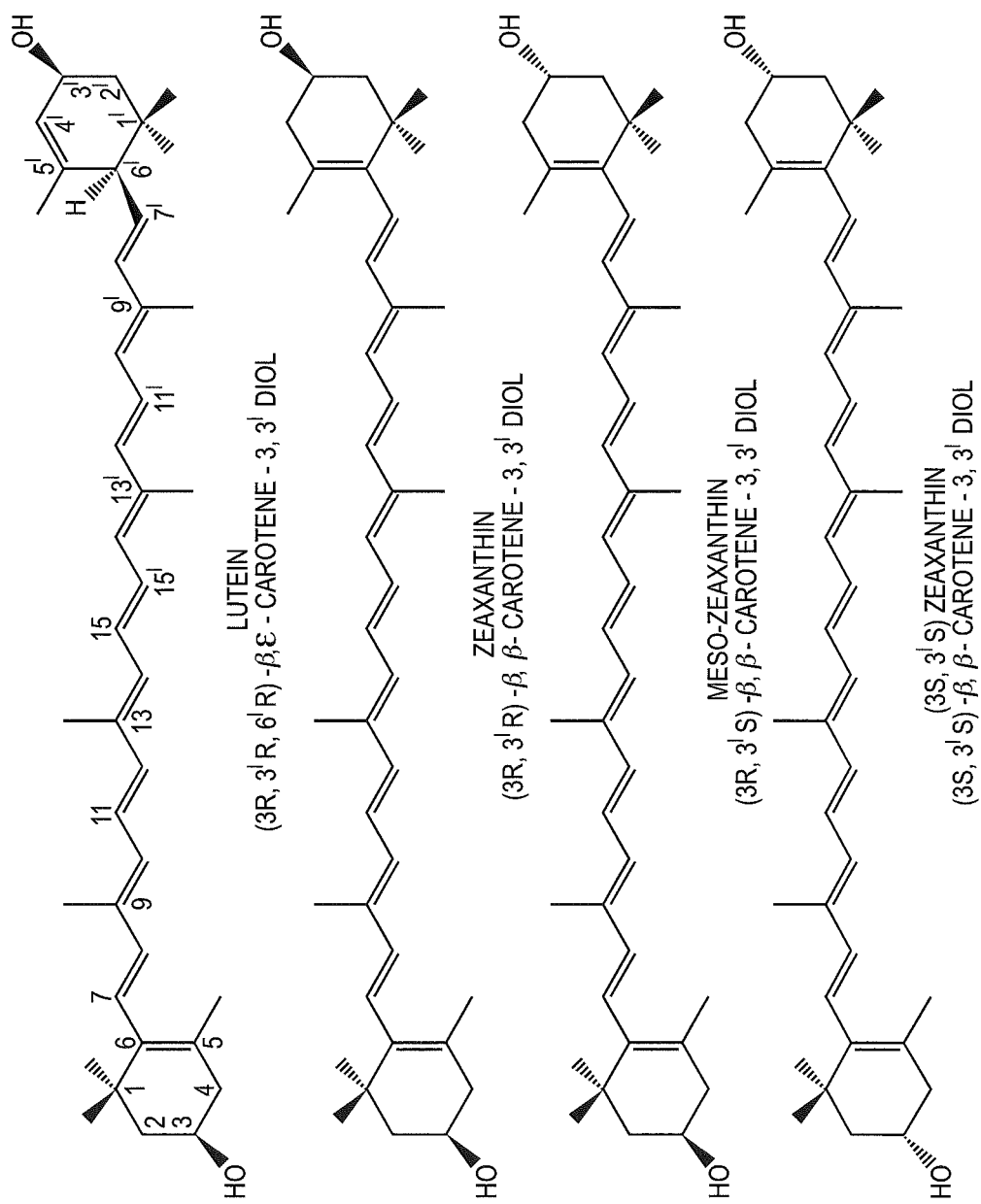
FIG. 1 is a schematic representation of the structural formulae for lutein, zeaxanthin and meso-zeaxanthin.

This example relates to a scientific research study conducted at the Nutrition Research Centre Ireland (NRCI).

Patients with AD were recruited from the University Hospital Waterford (UHW) via the Age-Related Care Unit department. This study was conducted in accordance with full sensitivity to the ethical requirements of the patients recruited. The study objectives and methodology complied fully with the widely-recognized international text and codes of practice, such as the Declaration of Helsinki and Good Research Practice. A protocol was developed specifically for this study to ensure that informed consent was obtained appropriately, and in keeping with the ethical code germane to obtaining consent from vulnerable subjects such as patients with AD.

In brief, the inventors performed three trial experiments. Two trials were conducted in patients with AD and one trial experiment in age-matched control subjects (free of AD).

In trial group 1, patients with AD (n=12) were given a daily dietary supplement containing macular carotenoids, but no omega-3 fatty acid. The supplement took the form of a capsule of a commercially-available preparation ("Macushield"™). Each capsule comprises approximately 10 mg lutein ("L"), 10 mg meso-zeaxanthin ("MZ") and 2 mg zeaxanthin ("Z"). One capsule per day was administered, under the supervision of the patients' carers, over a period of 18 months.

In trial group 2 (n=13) AD patients took a daily dietary supplement essentially identical to that used in trial group 1, but additionally containing 1 gm of fish oil (containing approximately 430 mg DHA and 90 mg EPA). The fish oil was of high quality and obtained from Epax® (Epax Norway AS, Alesund, Norway). Again, consumption of the supplement was overseen by the patients' carers, and continued over a period of 18 months.

The third trial group (n=31) were age-matched controls with no evidence of dementia. This group did not consume any dietary supplement.

All subjects were assessed at the start of the trial to provide a baseline. Characteristics assessed included, depending on the trial group, some/most of the following:
(i) serum concentration of L, Z and MZ;
(ii) macular pigment (MP) concentration in the macula, at 0.23 degrees of retinal eccentricity ("MP 0.23") (for explanation see below);
(iii) MP volume (MP volume under the curve) (—see below);
(iv) LPC 22:6 and LPC 20:5 (these are measures of the phospholipid in the blood containing either DHA or EPA respectively—see below); and
(v) medical assessment of dementia (+/−"MMSE"). The baseline values for these characteristics are shown in Table 1 below.

MP was measured by dual-wavelength autofluorescence (AF) using the Spectralis HRA+OCT MultiColor instrument (Heidelberg Engineering GmbH, Heidelberg, Germany), as described by Akuffo et al., (2014 Ophthalmic Epidemiol. 21, 111-123). Pupillary dilation was performed prior to measurement and patient details were entered into the Heidelberg Eye Explorer (HEYEX) version 1.7.1.0 software. Dual-wavelength AF in this device uses two excitation wavelengths, one that is well absorbed by MP (486 nm, blue), and one that is not (518 nm, green) (Trieschmann et al., 2006, Graefes Arch. Clin. Exp. Ophthalmol. 244, 1565-1574; Dennison et al., 2013 Exp. Eye Res. 116, 190-198). The following acquisition parameters were used: high speed scan resolution, two seconds cyclic buffer size, internal fixation, 30 seconds movie and manual brightness control. Alignment, focus and illumination were first adjusted in infrared mode. Once the image was evenly illuminated, the laser mode was switched from infrared to blue plus green laser light AF. Using the HEYEX software, the movie images were aligned and averaged, and a MP density map was created. MP volume was calculated as MP average times the area under the curve out to 7° eccentricity.

LPC 22:6 and LPC 20:5 assays were performed as follows: samples were extracted and analysed as previously published (Koulman, et al. 2014. "*The development and validation of a fast and robust dried blood spot based lipid profiling method to study infant metabolism*". Metabolomics 10:1018-25). All samples were infused into an Exactive Orbitrap (Thermo, Hemel Hempstead UK), using a Triversa Nanomate (Advion, Ithaca US).

TABLE 1

Demographics and health variables for patients in Trials 1-3 at baseline

| Demographics and health variables | Trial 1 (n = 12) AD | Trial 2 (n = 13) AD | Trial 3 (n = 31): Controls |
|---|---|---|---|
| Age (years) | 78.5 ± 8.754 | 78.77 ± 7.65 | 76 ± 6.6 |
| Sex (% females) | 6 (50%) | 8 (71%) | 13 (42%) |
| Serum lutein (μmol/L) | 0.261 ± 0.142 | 0.154 ± 0.084 | 0.297 ± 0.179 |
| Serum zeaxanthin (μmol/L) | 0.048 ± 0.035 | 0.062 ± 0.031 | 0.074 ± −0.179 |
| MMSE | 19 ± 2.89 | 16 ± 2.873 | 29 ± 0.179 |
| Category Mild AD | 4 (33%) | 2 (15%) | na |
| Category Moderate AD | 8 (67%) | 10 (77%) | na |
| Category Severe AD | 0 (0%) | 1 (8%) | na |
| MP 0.23 | 0.41 ± 0.24 | — | 0.57 ± 0.17 |
| MP Volume | 4114 ± 2308 | — | 6326 ± 2258 |

TABLE 1-continued

Demographics and health variables for patients in Trials 1-3 at baseline

| Demographics and health variables | Trial 1 (n = 12) AD | Trial 2 (n = 13) AD | Trial 3 (n = 31): Controls |
|---|---|---|---|
| LPC 22:6 (phospholipid containing DHA) | — | 0.160 ± 0.118 | |
| LPC 20:5 (phospholipid containing EPA) | — | 0.153 ± 0.144 | |

MMSE = Mini Mental State Examination; MP 0.23 = macular pigment at center (0.23 degrees of retinal eccentricity);
MP volume = macular pigment volume under the curve.
LPC 22:6 (phospholipid containing DHA) relative to the total lipid signal in blood. This is an excellent biomarker of DHA.
LPC 20:5 phospholipid containing EPA) = phospholipid containing EPA relative to the total lipid signal in blood. This is an excellent biomarker of EPA.

Method of Assessment
Biochemical Response:

For biochemical assessment, samples were obtained at baseline and also after 6 months of supplementation. Serum MZ, L and Z concentrations were assessed by high performance liquid chromatography (HPLC) of blood plasma. Markers of DHA and EPA were assessed by liquid chromatography (LC-)mass spectrometry (MS) metabolomics and lipidomics analysis of blood samples, using previously validated methods as detailed above.

MMSE:

This was performed under the supervision of a consultant clinician and is a validated technique. The results of the MMSE were used to guide the diagnosis of AD during patient recruitment. AD status was defined as follows: MMSE score 0-10=severe AD; MMSE score 11-20=moderate AD; MMSE score 21-25=mild AD; $26^+$=no AD. In addition to the MMSE conducted at the start of the trial, each patient was assessed for health and AD status at 18 months where possible.

Results
Macular Carotenoid Levels

Firstly, it should be noted that the average serum lutein concentration in Trial 2 subjects (0.154±0.084 μmol/L) was considerably lower than in the control group (0.297±0.179)—this difference was statistically significant ($p=0.010$) as determined by the Independent Samples T-test.

Figure 2:
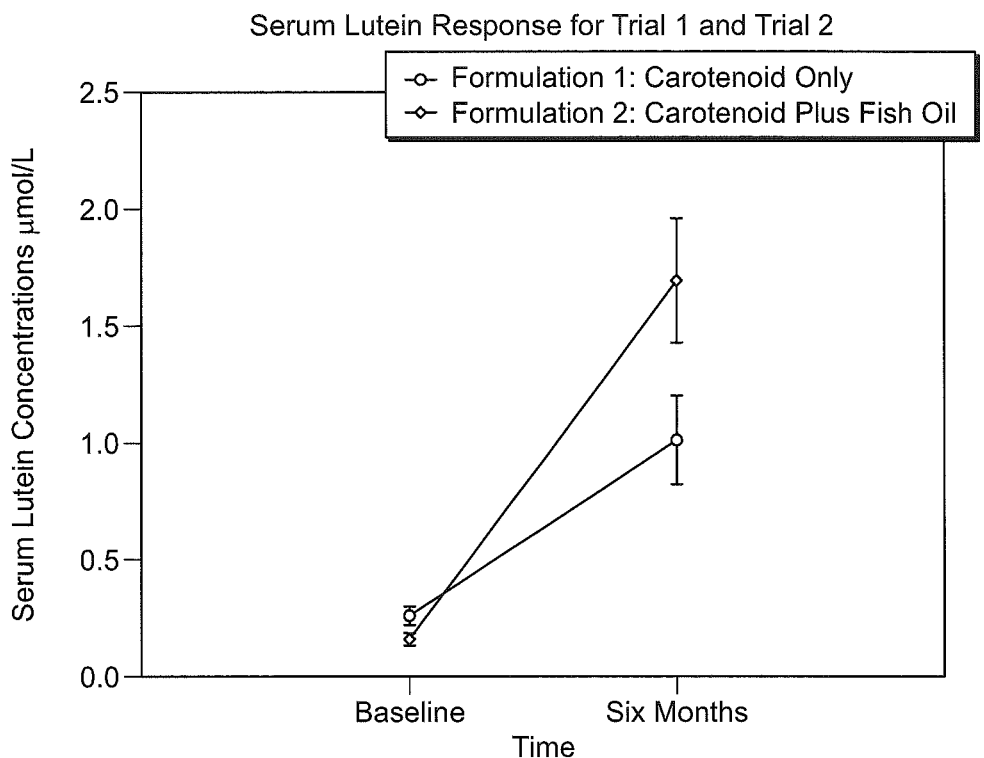
FIG. 2 is a graph of serum lutein concentration (μmol/L) against time (months)

FIG. 2 shows the mean serum lutein concentrations at the start of the trial and after 6 months for trial group 1 (filled circles) and trial group 2 (empty circles). It is readily apparent the serum lutein concentration increased over the 6 month period for both groups. However, the group 2 subjects (receiving the MC and fish oil supplement) exhibited a markedly superior increase in serum lutein, which was statistically significant ($p=0.002$).

Figure 3:
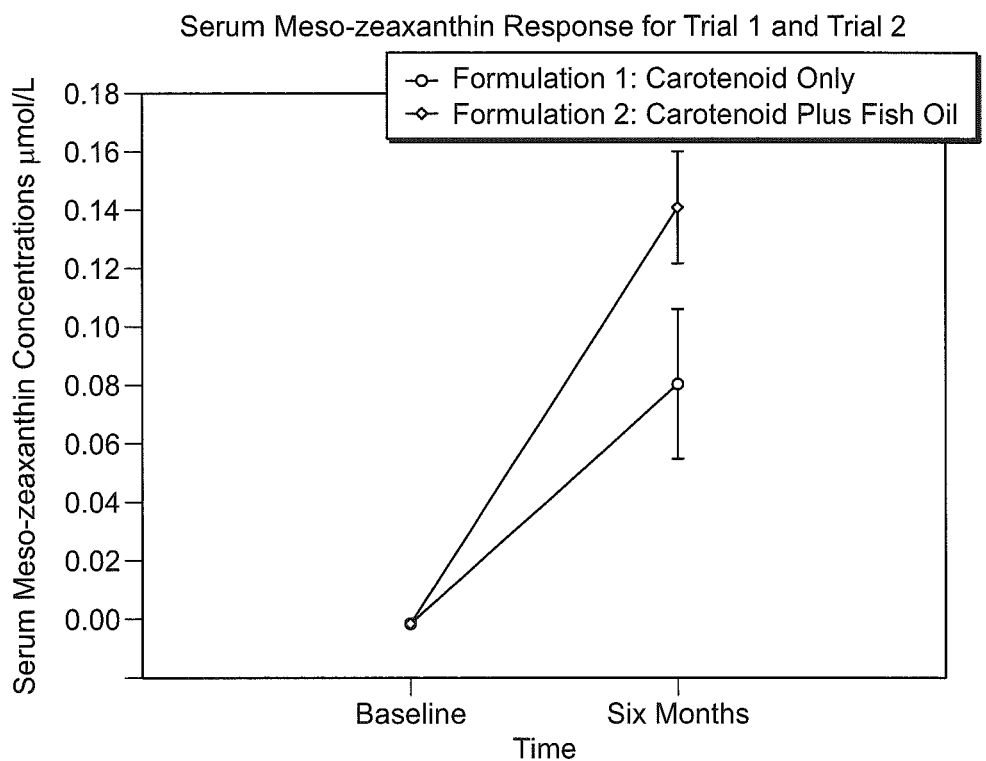
FIG. 3 is a graph of serum meso-zeaxanthin concentration (μmol/L) against time (months)

A similar picture was found for serum levels of MZ in the trial group 1 and 2 subjects (see FIG. 3): both groups exhibited a clear increase in serum MZ at 6 months compared to baseline; but the trial group 2 subjects displayed a greater increase than group 1 subjects, which was again statistically significant ($p=0.06$).

Omega-3 Fatty Acid Response

Figure 4:
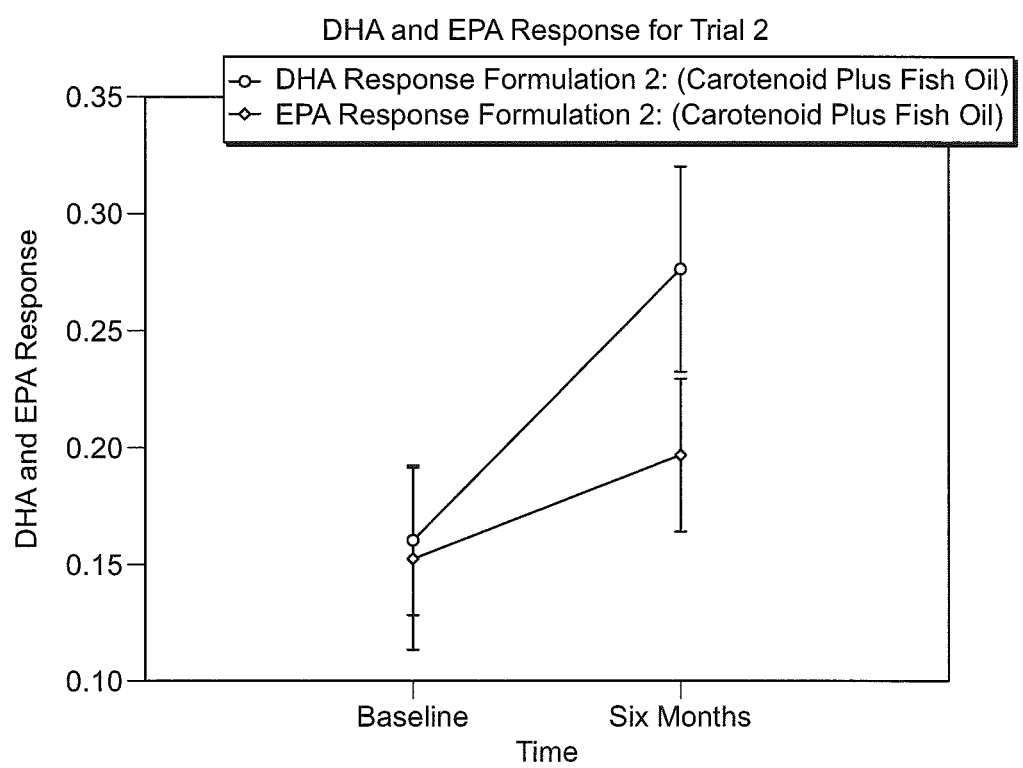
FIG. 4 is a graph of either DHA or EPA response (arbitrary units) against time (months).

The results for the serum DHA (filled circles) and serum EPA (empty circles) are shown in FIG. 4 for the trial group 2 subjects at baseline and after 6 months. It can be seen that the EPA concentration increased, and the concentration of DHA increased quite markedly. The greater response in DHA levels was to be expected, as the fish oil supplement used in the trial contained more DHA than EPA.

Medical Response

Patient medical assessment was performed at baseline and after 18 months of supplementation. Medical assessment was performed by a qualified AD nurse under the supervision of a medical consultant. Also, the patient carer was interviewed after 18 months of the patient being on the supplement. AD status at baseline was confirmed by the medical consultant.

Figure 6:
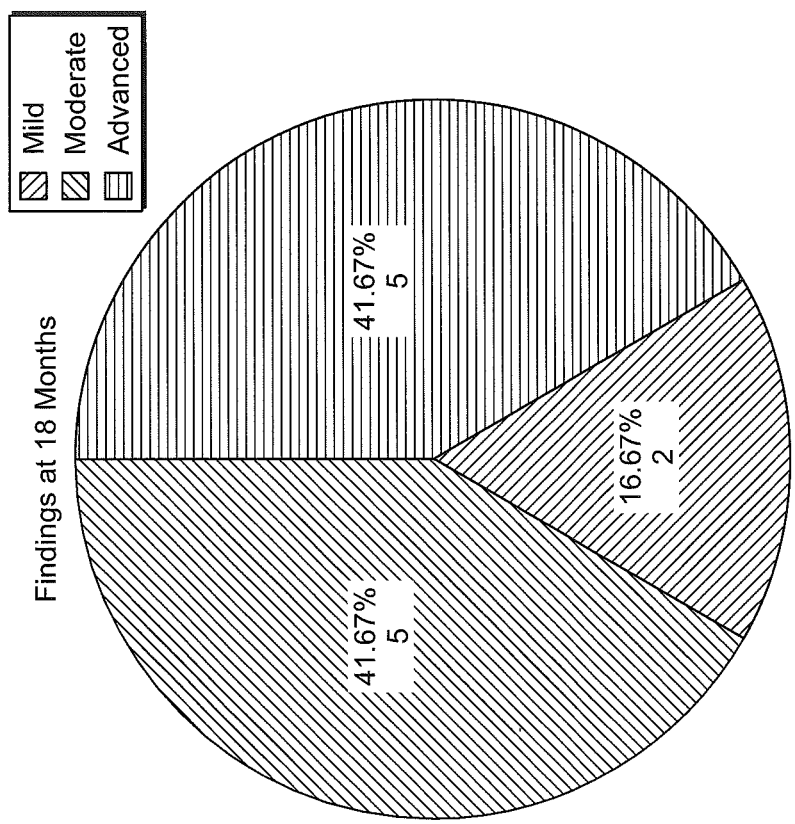
FIGS. 5-8 are pie charts illustrating the severity of dementia symptoms in patients at 0 months or at 18 months.
Figure 5:
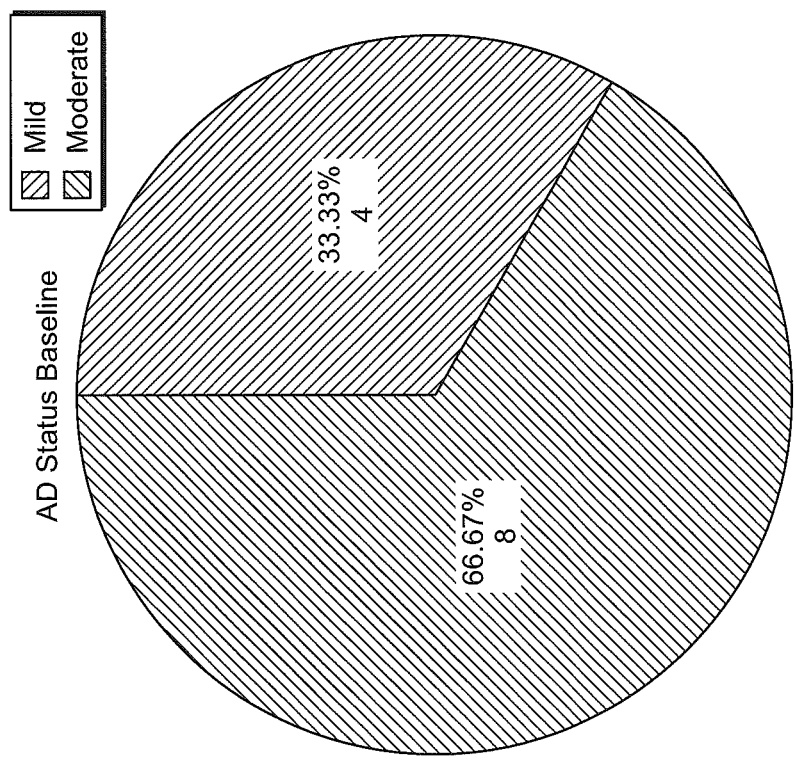
Figure 8:
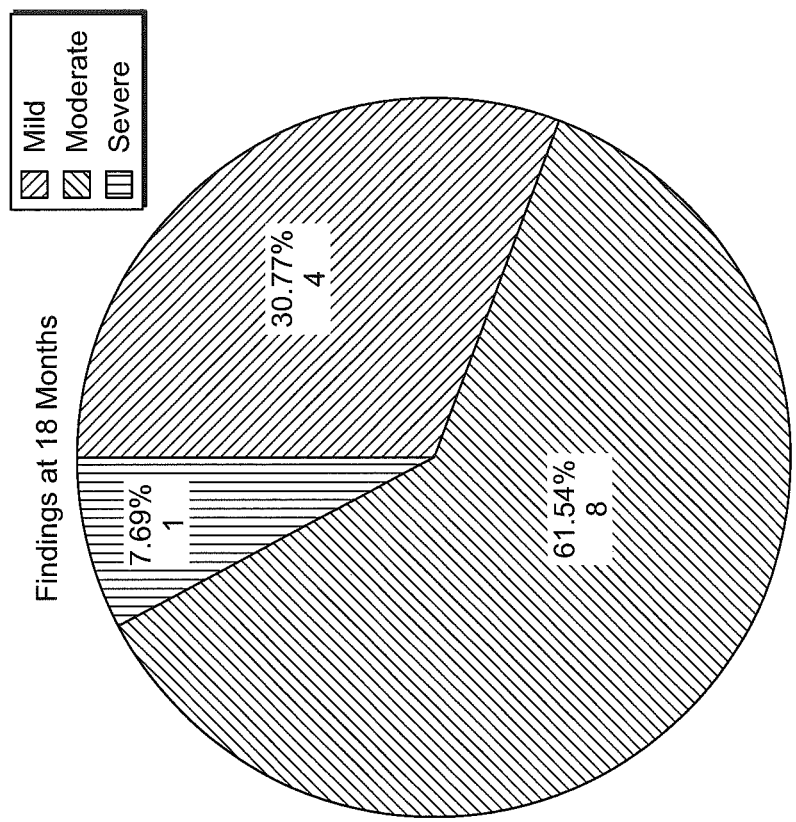
Figure 7:
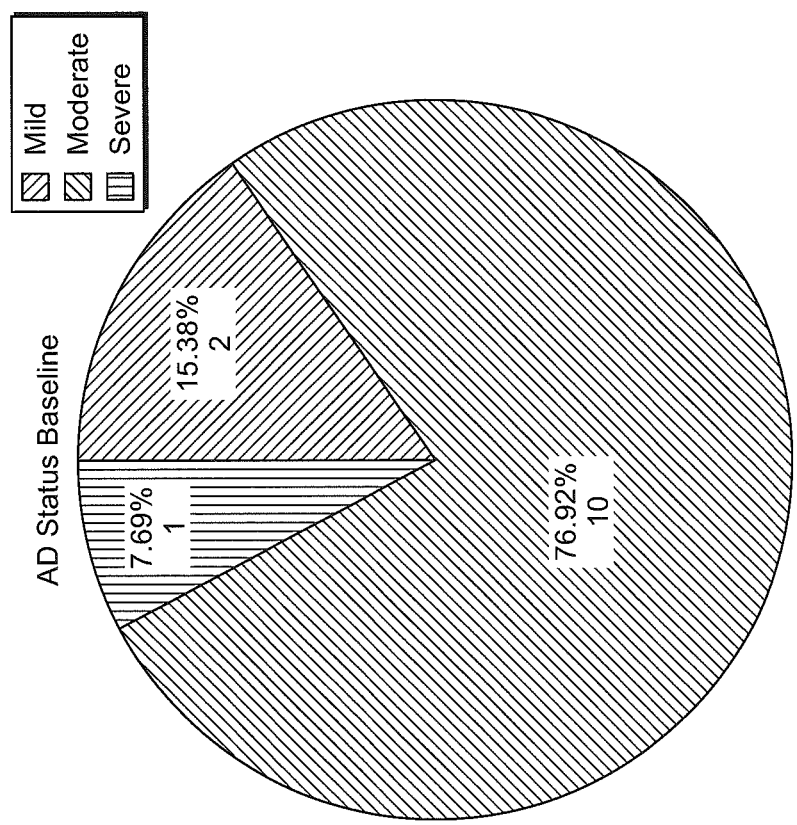

FIGS. 5 and 6 show the AD status for the trial group 1 subjects at baseline (FIG. 5) and at 18 months (FIG. 6). FIGS. 7 and 8 show the AD status for the trial group 2 subjects at baseline (FIG. 7) and at 18 months (FIG. 8).

In addition, the individual subject data for the two trial groups are presented in Table 2.

TABLE 2

Individual subject data

| Study | Subject ID | Age (years) | Sex (M—male; F = Female) | Baseline MMSE score | Baseline AD Status | Baseline Serum L (μmol/L) | 6-months Serum L (μmol/L) |
|---|---|---|---|---|---|---|---|
| Trial 1 | ADCD2 | 78 | M | 16 | Moderate | 0.072 | 0.666 |
| | ADCD3 | 81 | M | 17 | Moderate | 0.432 | 0.933 |
| | ADCD4 | 84 | M | 18 | Moderate | 0.302 | 0.973 |
| | ADCD5 | 82 | F | 23 | Mild | 0.466 | 0.676 |
| | ADCD8 | 90 | F | 15 | Moderate | 0.149 | 0.564 |
| | ADCD9 | 76 | M | 22 | Mild | 0.325 | 1.631 |
| | ADCD11 | 68 | F | 19 | Moderate | 0.397 | 0.941 |
| | ADN24 | 68 | M | 23 | Mild | 0.149 | 0.285 |
| | ADN25 | 64 | F | 15 | Moderate | 0.202 | 0.771 |
| | ADN26 | 74 | F | 21 | Mild | 0.364 | 1.972 |
| | ADN29 | 87 | F | 19 | Moderate | 0.238 | 2.415 |
| | ADN31 | 90 | M | 20 | Moderate | 0.034 | 0.364 |
| Trial 2 | C3A4 | 79 | F | 12 | Moderate | 0.051 | 0.548 |
| | C3A5 | 78 | M | 22 | Mild | 0.204 | 1.733 |
| | C3A6 | 89 | F | 14 | Moderate | 0.273 | 3.599 |
| | C3A7 | 81 | F | 13 | Moderate | 0.095 | 2.515 |
| | C3A8 | 87 | M | 17 | Moderate | 0.153 | 1.021 |

TABLE 2-continued

Individual subject data

| | | | | | | | |
|---|---|---|---|---|---|---|---|
| C3A9 | 88 | F | | 21 | Mild | 0.122 | 0.536 |
| C3A10 | 71 | F | | 18 | Moderate | 0.107 | 2.722 |
| C3A12 | 79 | F | | 17 | Moderate | 0.244 | 2.229 |
| C3A13 | 77 | M | | 110 | Severe | 0.064 | 1.971 |
| C3A14 | 69 | M | | 17 | Moderate | 0.074 | 0.342 |
| C3A16 | 87 | M | | 18 | Moderate | 0.123 | 0.974 |
| C3A17 | 74 | F | | 18 | Moderate | 0.315 | 1.879 |
| C3A19 | 65 | F | | 18 | Moderate | 0.182 | 1.97 |

| Study | Subject ID | Baseline Serum Z ($\mu$mol/L) | 6-months Serum Z ($\mu$mol/L) | 6-months Serum MZ ($\mu$mol/L) | Observations at 18-months |
|---|---|---|---|---|---|
| Trial 1 | ADCD2 | 0.006 | 0.062 | 0.08 | No difference reported |
| | ADCD3 | 0.046 | 0.088 | 0.044 | No difference reported |
| | ADCD4 | 0.057 | 0.099 | 0.052 | No difference reported |
| | ADCD5 | 0.133 | 0.099 | 0.034 | No difference reported |
| | ADCD8 | 0.032 | 0.056 | 0.043 | Disease advanced; patient too sick to continue study |
| | ADCD9 | 0.076 | 0.189 | 0.086 | Disease advanced; patient in a nursing home |
| | ADCD11 | 0.057 | 0.076 | 0.044 | No information available |
| | ADN24 | 0.054 | 0.041 | 0.014 | No difference reported |
| | ADN25 | 0.035 | 0.078 | 0.027 | Disease advanced; patient unable to continue study |
| | ADN26 | 0.059 | 0.248 | 0.294 | Disease advanced; patient unable to follow instruction |
| | ADN29 | 0.02 | 0.245 | 0.234 | Disease advanced; patient too sick to continue study |
| | ADN31 | 0.003 | 0.024 | 0.018 | No difference reported |
| Trial 2 | C3A4 | 0.027 | 0.057 | 0.062 | Carer reported good improvement to memory |
| | C3A5 | 0.05 | 0.145 | 0.1 | Carer reported good improvement to sight |
| | C3A6 | 0.089 | 0.312 | 0.228 | Carer reported subject was improved and manageable |
| | C3A7 | 0.041 | 0.226 | 0.153 | No difference reported |
| | C3A8 | 0.058 | 0.094 | 0.091 | No difference reported |
| | C3A9 | 0.069 | 0.082 | 0.03 | No difference reported |
| | C3A10 | 0.026 | 0.244 | 0.186 | No difference reported |
| | C3A12 | 0.075 | 0.153 | 0.152 | Carer reported good improvement to vision |
| | C3A13 | 0.044 | 0.131 | 0.178 | No difference reported |
| | C3A14 | 0.048 | 0.039 | 0.1 | No difference reported |
| | C3A16 | 0.043 | 0.058 | 0.085 | Carer reported good improvement to memory |
| | C3A17 | 0.137 | 0.065 | 0.252 | No difference reported |
| | C3A19 | 0.105 | 0.148 | 0.226 | Carer reported good improvement to vision |

As seen from the pie charts (FIGS. 5 and 6, data from Trial 1, carotenoid only intervention) and Table 2, progression of AD was evident in this group over the 18 month period, with 42% of patients' health status dropping to the point that they could not continue in the trial. Reasons for dropout include: patient moved into a nursing home due to AD progressing; patient became too unwell to continue; cognitive decline too severe; no longer able to follow instructions.

However, as seen in FIGS. 7 and 8, (data from Trial 2, carotenoid and fish oil Aintervention) and Table 2, progression of AD was very markedly less, with carers reporting improved cognitive function, visual function and general wellness. Of note, no patients dropped out of Trial 2 and the comments received were as follows: memory improvement, eyesight improvement, AD didn't get worse.

CONCLUSIONS

The examples provided here suggest that AD may be a nutrient-deficiency disease. The nutrients in question are the carotenoids (lutein and zeaxanthin) and DHA, which have been identified in the human brain. These nutrients have the potential to support brain health and reduce risk of AD via their antioxidant, anti-inflammatory, and structural roles. The inventors hypothesise that AD is a nutrient-deficiency disease, and that the positive medical responses observed in the trials are due to correction of this deficiency. However, in circumstances where the disease is developed, the correction of the nutrient deficiency is not capable to reverse the disease; but, stabilization of brain health ad function is achieved, consistent with halting AD progression in patients supplemented with carotenoids and fish oil.

The inventors suggest that AD is a deficiency disease of two nutrient components: a. the macular pigments lutein and zeaxanthin, which are obtained from eating green leafy vegetables (e.g. spinach and kale) and b. DHA, obtained from eating fatty fish (e.g. salmon).

The data shows that AD can be prevented by a satisfactory intake of, e.g. the abovementioned foods.

REFERENCES

[1] Alzheimer's Association (2017) 2017 *Alzheimer's disease facts and figures*, Alzheimer's Association, Chicago, Ill., USA.

[2] Tangney et al., (2011) Adherence to a Mediterranean-type dietary pattern and cognitive decline in a community population. *Am J Clin Nutr* 93, 601-607.
[3] Feart et al., (2009) Adherence to a Mediterranean diet, cognitive decline, and risk of dementia. *J.A.M.A.* 302, 638-648.
[4] Trichopoulou et al., (2015) Mediterranean diet and cognitive decline over time in an elderly Mediterranean population. *Eur. J Nutr.* 54, 1311-1321.
[5] Pelletier et al., (2015) Mediterranean diet and preserved brain structural connectivity in older subjects. *Alzheimers Dement* 11, 1023-1031.
[6] McEvoy et al., (2017) Neuroprotective Diets Are Associated with Better Cognitive Function: The Health and Retirement Study. *J Am Geriatr Soc* 65, 1857-1862.
[7] Lourida et al., (2013) Mediterranean diet, cognitive function, and dementia: a systematic review. *Epidemiology* 24, 479-489.
[8] Psaltopoulou et al., (2013) Mediterranean diet, stroke, cognitive impairment, and depression: A meta-analysis. *Ann Neurol* 74, 580-591.
[9] Singh et al., (2014) Association of mediterranean diet with mild cognitive impairment and Alzheimer's disease: a systematic review and meta-analysis. *J Alzheimers Dis* 39, 271-282.
[10] Scarmeas et al., (2006) Mediterranean diet and risk for Alzheimer's disease. *Ann Neurol* 59, 912-921.
[11] Scarmeas et al., (2009) Mediterranean diet and mild cognitive impairment. *Arch Neurol* 66, 216-225.
[12] Sofi et al., (2014) Mediterranean diet and health status: an updated meta-analysis and a proposal for a literature-based adherence score. *Public Health Nutr* 17, 2769-2782.
[13] Muldoon et al., (2014) Long-chain omega-3 fatty acids and optimization of cognitive performance. *Mil Med* 179, 95-105.
[14] Cole et al., (2005) Prevention of Alzheimer's disease: Omega-3 fatty acid and phenolic anti-oxidant interventions. *Neurobiol Aging* 26 Suppl 1, 133-136.
[15] Fotuhi et al., (2009) Fish consumption, long-chain omega-3 fatty acids and risk of cognitive decline or Alzheimer disease: a complex association. *Nat Clin Pract Neurol* 5, 140-152.
[16] Thomas et al., (2015) Omega-3 Fatty Acids in Early Prevention of Inflammatory Neurodegenerative Disease: A Focus on Alzheimer's Disease. *Biomed Res Int* 2015, 172801.
[17] Cole & Frautschy et al., (2010) DHA may prevent age-related dementia. *J Nutr* 140, 869-874.
[18] Abubakari A R, Naderali M M, Naderali E K (2014) Omega-3 fatty acid supplementation and cognitive function: are smaller dosages more beneficial? *Int J Gen Med* 7, 463-473.
[19] Yurko-Mauro et al., (2010) Beneficial effects of docosahexaenoic acid on cognition in age-related cognitive decline. *Alzheimers Dement* 6, 456-464.
[20] Phillips et al., (2015) No Effect of Omega-3 Fatty Acid Supplementation on Cognition and Mood in Individuals with Cognitive Impairment and Probable Alzheimer's Disease: A Randomised Controlled Trial. *Int J Mol Sci* 16, 24600-24613.
[21] van de Rest et al., (2008) Effect of fish oil on cognitive performance in older subjects: a randomized, controlled trial. *Neurology* 71, 430-438.
[22] Perry et al., (2009) Xanthophyll (lutein, zeaxanthin) content in fruits, vegetables and corn and egg products. *Journal of Food Composition and Analysis* 22, 9-15.
[23] Johnson et al., (2013) Relationship between Serum and Brain Carotenoids, alpha-Tocopherol, and Retinol Concentrations and Cognitive Performance in the Oldest Old from the Georgia Centenarian Study. *J Aging Res* 2013, 951786.
[24] Craft et al., (2004) Carotenoid, tocopherol, and retinol concentrations in elderly human brain. *J Nutr Health Aging* 8, 156-162.
[25] Feart et al., (2016) Plasma Carotenoids Are Inversely Associated With Dementia Risk in an Elderly French Cohort. *J Gerontol A Biol Sci Med Sci* 71, 683-688.
[26] Min & Min (2014) Serum lycopene, lutein and zeaxanthin, and the risk of Alzheimer's disease mortality in older adults. *Dement Geriatr Cogn Disord* 37, 246-256.
[27] Loef & Walach (2012) Fruit, vegetables and prevention of cognitive decline or dementia: a systematic review of cohort studies. *J Nutr Health Aging* 16, 626-630.
[28] Hammond et al., (2017) Effects of Lutein/Zeaxanthin Supplementation on the Cognitive Function of Community Dwelling Older Adults: A Randomized, Double-Masked, Placebo-Controlled Trial. *Front Aging Neurosci* 9, 254.
[29] Johnson et al., (2008) Cognitive findings of an exploratory trial of docosahexaenoic acid and lutein supplementation in older women. *Nutr Neurosci* 11, 75-83.
[30] Chew et al., Age-Related Eye Disease Study 2 Research G (2015) Effect of Omega-3 Fatty Acids, Lutein/Zeaxanthin, or Other Nutrient Supplementation on Cognitive Function: The AREDS2 Randomized Clinical Trial. *JAMA* 314, 791-801.
[31] Mangialasche et al., (2010) High plasma levels of vitamin E forms and reduced Alzheimer's disease risk in advanced age. *J Alzheimers Dis* 20, 1029-1037.
[32] Livingstone et al., (2017) Dementia prevention, intervention, and care. *Lancet* 390, 2673-2734.

The invention claimed is:

1. A method for preventing or retarding the progression of cognitive impairment in a human subject exhibiting cognitive impairment due to dementia, the method comprising the step of administering an effective amount of a composition comprising each of lutein, zeaxanthin and meso-zeaxanthin; and a composition comprising at least one omega-3 fatty acid, wherein the human subject to be treated has a mini mental state examination (MMSE) score of 25 or less.

2. The method according to claim 1, wherein a single administered composition comprises each of lutein, zeaxanthin, meso-zeaxanthin and at least one omega-3 fatty acid.

3. The method according to claim 1, wherein the said at least one omega-3 fatty acid is docosahexaenoic acid.

4. The method according to claim 1, wherein the said at least one omega-3 fatty acid is provided in the composition as a fish oil.

5. The method according to claim 1, wherein the said at least one omega-3 fatty acid comprises at least two omega-3 fatty acids.

6. The method according to claim 1, wherein the omega-3 fatty acid-containing composition comprises docosahexaenoic acid and eicosapentaenoic acid.

7. The method according to claim 1, wherein the said at least one omega-3 fatty acid is provided as the free acid, as a salt or as a triglyceride.

8. The method according to claim 7, wherein the salt comprises a monocation.

9. The method according to claim 7, wherein the salt comprises a metal monocation.

10. The method according to claim 1, wherein the composition/s is/are administered orally to the subject at least three times a week.

11. The method according to claim 1, wherein the composition/s is/are administered to the subject daily.

12. The method according to claim 1, wherein the composition/s is/are in unit dose form.

13. The method according to claim 12, wherein each unit dose of composition comprises about 10 mg meso-zeaxanthin, about 10 mg lutein, about 2 mg zeaxanthin, and fish oil containing said at least one omega-3 fatty acid.

14. The method according to claim 12, wherein each unit dose of composition comprises about 15 mg meso-zeaxanthin, about 5 mg lutein, about 1 mg zeaxanthin, and fish oil containing said at least one omega-3 fatty acid.

15. The method according to claim 12, wherein each unit dose of the composition comprises between about 20 mg and about 2 grams of docosahexaenoic acid.

16. The method according to claim 12, wherein each unit dose of composition comprises about 1 gram of fish oil containing said at least one omega-3 fatty acid.

17. The method according to claim 1, wherein the composition/s further comprise one or more of the following: acidity regulators; anticaking agents selected from the group consisting of sodium aluminosilicate, calcium or magnesium carbonate, calcium silicate, sodium and potassium ferricyanide; antioxidants selected from the group consisting of vitamin E, vitamin C, and polyphenols; colorings selected from the group consisting of artificial colorings FD&C Blue No. 1, Blue No. 2, Green No. 3, Red No. 40, Red No. 3, Yellow No. 5 and Yellow No. 6; and natural colorings selected from the group consisting of caramel, annatto, cochineal, betanin, turmeric, saffron, and paprika; color retention agents; emulsifiers; flavours; flavour enhancers; preservatives; stabilizers; sweeteners and thickeners.

18. The method according to claim 1, wherein the composition/s is/are in the form of a tablet or capsule.

19. The method according to claim 1, wherein the subject consumes the composition/s on a daily basis over a period of at least 12 months.

20. The method according to claim 1, comprising use of a composition consisting essentially of lutein, zeaxanthin, meso-zeaxanthin, at least one omega-3 polyunsaturated fatty acid or corresponding salt or triglyceride, and a diluent, carrier or excipient.

21. The method according to claim 20, wherein the omega-3 polyunsaturated fatty acid or corresponding salt or triglyceride is DHA or a salt or triglyceride of DHA.

22. The method according to claim 1, wherein the method comprises daily oral administration of a unit dose form composition comprising each of lutein; zeaxanthin; meso-zeaxanthin; and DHA and/or EPA, in preventing or retarding the progression of cognitive impairment in a subject already exhibiting one or more symptoms of Alzheimer's disease prior to administration of the composition.

* * * * *